(12) United States Patent
Madsen

(10) Patent No.: US 7,223,247 B2
(45) Date of Patent: May 29, 2007

(54) APPARATUS FOR DETERMINING A LOCATION IN A BODY USING A CATHETER AND METHOD OF USING SUCH CATHETER

(75) Inventor: Michael O. Madsen, Lynbgy (DK)

(73) Assignee: Medtronic, Inc., Minneapolis, MN (US)

( * ) Notice: Subject to any disclaimer, the term of this patent is extended or adjusted under 35 U.S.C. 154(b) by 300 days.

(21) Appl. No.: 10/698,348

(22) Filed: Nov. 1, 2003

(65) Prior Publication Data

US 2005/0096634 A1    May 5, 2005

(51) Int. Cl.
*A61B 5/00* (2006.01)

(52) U.S. Cl. ...................................... 600/561

(58) Field of Classification Search ........... 600/591, 600/593, 350, 343, 361, 459, 463, 561; 606/196, 606/139, 140; 128/903, 205.23, 207.14
See application file for complete search history.

(56) References Cited

U.S. PATENT DOCUMENTS

| | | | | |
|---|---|---|---|---|
| 4,981,470 A | * | 1/1991 | Bombeck, IV | 600/350 |
| 5,247,938 A | * | 9/1993 | Silverstein et al. | 600/459 |
| 5,433,216 A | * | 7/1995 | Sugrue et al. | 600/591 |
| 6,285,897 B1 | * | 9/2001 | Kilcoyne et al. | 600/350 |
| 6,464,708 B1 | * | 10/2002 | Higuma et al. | 606/140 |

FOREIGN PATENT DOCUMENTS

WO    WO 00/59376    10/2000

OTHER PUBLICATIONS

Sandhill Scientific, Inc., "The Sandhill Scientific Solution", Second Trimester 2002, vol. V, Issue 2, pp. 1-7.
Diederich, Linda, "Esophageal Manometry Procedure", Ch. IV, pp. 41-56.
Diederich, Linda, "Technical Aspects of pH Monitoring", Ch. XV, pp. 185-196.
Sandhill Scientific, Inc., "What's New at Sandhill Scientific", two pages.
Medtronic, Inc., Bravo™ pH Monitoring System, A patient-friendly test for heartburn, one page.
Medtronic, Inc., "Digitrapper™ pH, Ambulatory 24-Hour pH Recorder", 2000, two pages.
Medtronic, Inc., "Bravo™ pH Monitoring System, Catheter-Free pH Testing", 2002, two pages.

* cited by examiner

*Primary Examiner*—Max F. Hindenburg
*Assistant Examiner*—Brian Szmal
(74) *Attorney, Agent, or Firm*—IPLM Group, P.A.

(57) ABSTRACT

Method of using an esophageal catheter. A distal end of the catheter is passed through the esophagus into the stomach of a patient. A constant pressure of gas is applied to the catheter. The back pressure of the gas is measured. The distal end of the catheter is pulled from the patient. An increase in the pressure measured is noted. A subsequent decrease in the pressure measured is then noted. The upper boundary of the lower esophageal sphincter is identified as a function of such decrease. The catheter is then used to place a remote monitoring device to the esophagus.

18 Claims, 4 Drawing Sheets

APPARATUS FOR DETERMINING A LOCATION IN A BODY USING A CATHETER AND METHOD OF USING SUCH CATHETER

FIELD OF THE INVENTION

The present invention relates generally medical devices and, more particularly, to catheters and use of catheters to determine a location in a body, preferably in conjunction with attachment of a monitoring device in the body.

BACKGROUND OF THE INVENTION

Gastroesophageal reflux occurs when stomach acid intermittently surges into the esophagus. It is common for most people to experience acid reflux activity occasionally as heartburn. Gastroesophageal reflux disease (GERD) is a clinical condition in which the reflux of stomach acid into the esophagus is frequent enough and severe enough to impact a patient's normal functioning or to cause damage to the esophagus.

In the lower part of the esophagus, where the esophagus meets the stomach, there is a muscular valve called the lower esophageal sphincter (LES). Normally, the LES relaxes to allow food to enter into the stomach from the esophagus. The LES then contracts to prevent stomach acids from entering the esophagus. In GERD, the LES relaxes too frequently or at inappropriate times allowing stomach acids to reflux into the esophagus.

The most common symptom of GERD is heartburn. Acid reflux also leads to esophageal inflammation, which causes symptoms such as painful swallowing and difficulty swallowing. Pulmonary symptoms such as coughing, wheezing, asthma, or inflammation of the vocal cords or throat may occur in some patients. More serious complications from GERD include esophageal ulcers and narrowing of the esophagus. The most serious complication from chronic GERD is a condition called Barrett's esophagus in which the epithelium of the esophagus is replaced with abnormal tissue. Barrett's esophagus is a risk factor for the development of cancer of the esophagus.

Accurate diagnosis of GERD is difficult but important. Accurate diagnosis allows identification of individuals at high risk for developing the complications associated with GERD. It is also important to be able to differentiate between gastroesophageal reflux, other gastrointestinal conditions, and various cardiac conditions. For example, the similarity between the symptoms of a heart attack and heartburn often lead to confusion about the cause of the symptoms.

One method of diagnosing GERD is to monitor the pH in the lower esophagus at or somewhat above the upper boundary of the lower esophageal sphincter.

Existing esophageal pH monitoring devices are often intubated nasally using a wired monitor. Such systems are often left in place for twenty-four hours or longer. Such systems are typically unpopular with patients who sometimes find the protrusion of a wire for such an extended period of time.

At least one other esophageal pH monitoring has been used which deposits a remote monitoring capsule in the esophagus of a patient using a catheter. The remote monitoring capsule transmits pH information from the esophagus to an external receiver and remains in place up to a day or longer before detaching from the esophagus and passing harmlessly through the digestive system.

In either of these esophageal pH monitoring systems, it is important to place the monitoring device in the proper location in the esophagus. Typically, the proper location is determined as a function of the lower esophageal sphincter. Since the most severe effects of GERD are found in the lower esophagus nearest the lower esophageal sphincter, it is important to be able to locate a location in the esophagus as a function of the lower esophageal sphincter.

Such a position can be located, for example, visually through the use of an endoscope. However, while some doctors are comfortable in the use of an endoscope, others, principally surgeons, typically rely on manometry to determine the proper location.

Conventionally, manometry is done trans-nasally since a trans-nasal intubation is typically considered less intrusive for the patient. Further, manometry is also typically done with water due to its compatibility with the patient and because it can provide accurate pressure measurements.

Manometry accomplished in this manner involves placing a catheter trans-nasally into the esophagus through the lower esophageal sphincter and into the stomach. Water at a pressure is applied through the lumen in the catheter and the distal end of the catheter is moved upwards through the lower esophageal sphincter. The pressure sensed from the applied water pressure will increase as the distal end of the catheter passes through the restricted area of the lower esophageal sphincter.

BRIEF SUMMARY OF THE INVENTION

A remote monitoring capsule can be intubated trans-orally due to the size of the capsule itself. The larger size of the capsule may make it difficult intubate such a capsule trans-nasally.

With a trans-oral intubation of a remote monitoring capsule, difficulties arise in attempting to locate the lower esophageal sphincter trans-nasally. If a trans-nasal manometry is attempted, it is difficult to translate the distance to the proper location determined trans-nasally to a distance needed to duplicate that location trans-orally. The distance to the proper location from the narres measured trans-nasally does not correlate well to the distance to the proper location from the incisors measured trans-orally. For this reason, it is desirable perform the manometry to find the proper location for the capsule through the same pathway used for the capsule. In other words, if the capsule is to be intubated trans-orally, then manometry to find the proper location for the capsule should also be done trans-orally.

The present invention takes advantage of an already existing catheter which is used for the placement of a remote monitoring capsule trans-orally near the upper boundary of the lower esophageal sphincter. The same catheter which will be used in placing the remote monitoring capsule can be intubated through the esophagus and lower esophageal sphincter into the stomach. A gas, typically air, at a constant pressure can be applied to the lumen of the catheter while the distal end of the catheter is in the stomach. The back pressure on the gas introduced through the lumen of the catheter will be relatively low in the relatively larger space of the stomach. The distal end of the catheter is then pulled backward, or out, through the lower esophageal sphincter. As the distal end of the catheter passes through the relatively restricted area of the lower esophageal sphincter, a relatively higher pressure will be observed on the gas introduced into the lumen of the catheter. Thus, the relative pressure exhibited by the gas introduced into the lumen of the catheter will at first increase due to the restriction caused by the lower esophageal sphincter and then decrease as the distal end of the catheter reaches the relatively larger space of the esophagus. The decrease in pressure following the initial increase in pressure marks the location of the upper boundary of the lower esophageal sphincter.

The proper location for the remote monitoring capsule can then be determined relative to the identified location of the upper boundary of the lower esophageal sphincter. As an example, if it is desired to place the remote monitoring capsule approximately five centimeters above the upper boundary of the lower esophageal sphincter, then the catheter would be pulled an additional five centimeters from the esophagus. In some cases, the actual location of the monitoring device may be somewhat different than the location of the outlet of the lumen of the catheter. For example, if the monitoring device is located two centimeters below the outlet of the lumen of the catheter, then the catheter should be pulled up an additional two centimeters, or seven centimeters total, to properly place the monitoring device five centimeters above the upper boundary of the lower esophageal sphincter.

Following the identification of the proper location of the remote monitoring capsule, the catheter used for the manometry to identify that location can be left in place and used according to conventional techniques to insert and place the remote monitoring capsule.

Due to the desired reuse of the lumen of the catheter, liquid, principally water, based manometry is not desirable. Use of a foreign substance, such as water, leaves open the possibility that some the substance will still remain in the lumen of the catheter following the manometry. The presence of such foreign substance could possibly compromise the proper placement of the remote monitoring capsule.

Thus a gas, usually air, is used in the trans-oral manometry using the same catheter as will be used to place the remote monitoring capsule. A gas, by it nature, is a compressible substance, and typically will provide less precise measurements in pressure than a more incompressible liquid. However, since only relative pressures are required to properly locate the upper boundary of the lower esophageal sphincter, air can be used with good results to properly locate the upper boundary of the lower esophageal sphincter.

DETAILED DESCRIPTION OF THE INVENTION

A remote physical parameter, for example pH, monitoring capsule suitable for insertion into the body, for example esophagus, is described in a PCT Patent Application Number PCT/US00/09445, Kilcoyne et al, Implantable Monitoring Probe, filed by Endonetics, Inc., published as International Publication Number WO 00/59376 on Oct. 12, 2000, the contents of which are hereby incorporated by reference.

Figure 1:
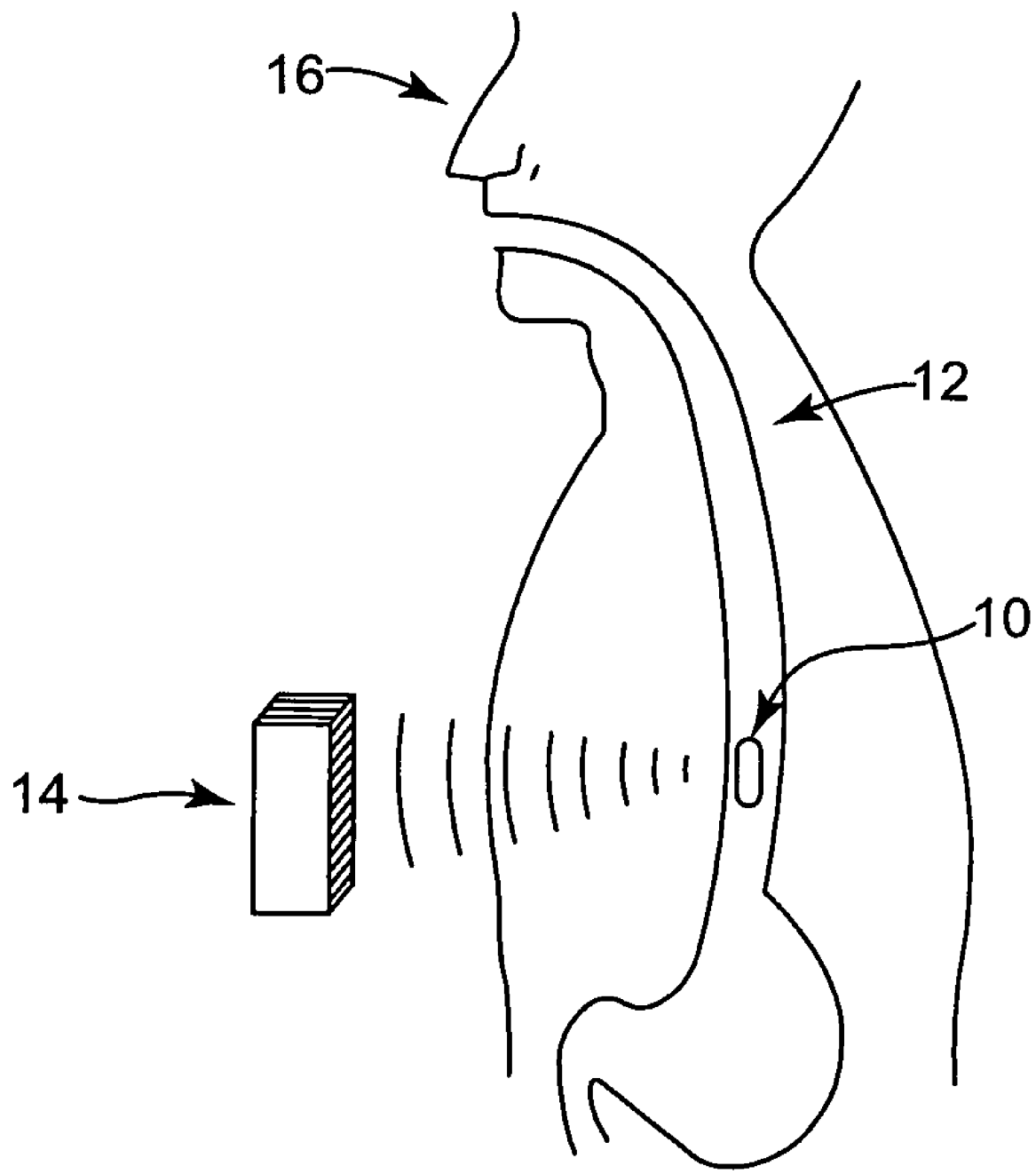
FIG. 1 is a schematic illustration of a remote pH monitor placed in an esophagus of a patient.

Physical parameter data can be relayed by monitor 10, which is positioned within the esophagus 12, to a radiofrequency receiver 14 located outside the body of a patient 16 (FIG. 1). Transmission of data can be accomplished via radio telemetry in real time. Radiofrequency receiver 14 can receive physiological parameter data within twelve seconds after it is measured by monitor 10. After reception of this data, radiofrequency receiver 14 can record, manipulate, interpret and/or display the data, using technology well known to those skilled in the art. Patient 16 can wear radiofrequency receiver 14 and recorder on, for example, a belt, bracelet, arm or leg band, or necklace during the period of pH study or other analysis.

Following monitoring, monitor 10 detaches from the wall of esophagus 12 and passes through the gastrointestinal track and is excreted in the stool. Detachment may occur, for example, from about two days to about ten days following attachment to the wall of esophagus 12.

A preferred method of placing monitor 10 in esophagus 12 is illustrated in copending U.S. patent application Ser. No. 10/424,550, filed Apr. 25, 2003, entitled Delivery Device For an Acidity Monitoring System, assigned to Medtronic, Inc., the assignee of the present application. The contents of this document are incorporated herein by reference.

Figure 2:
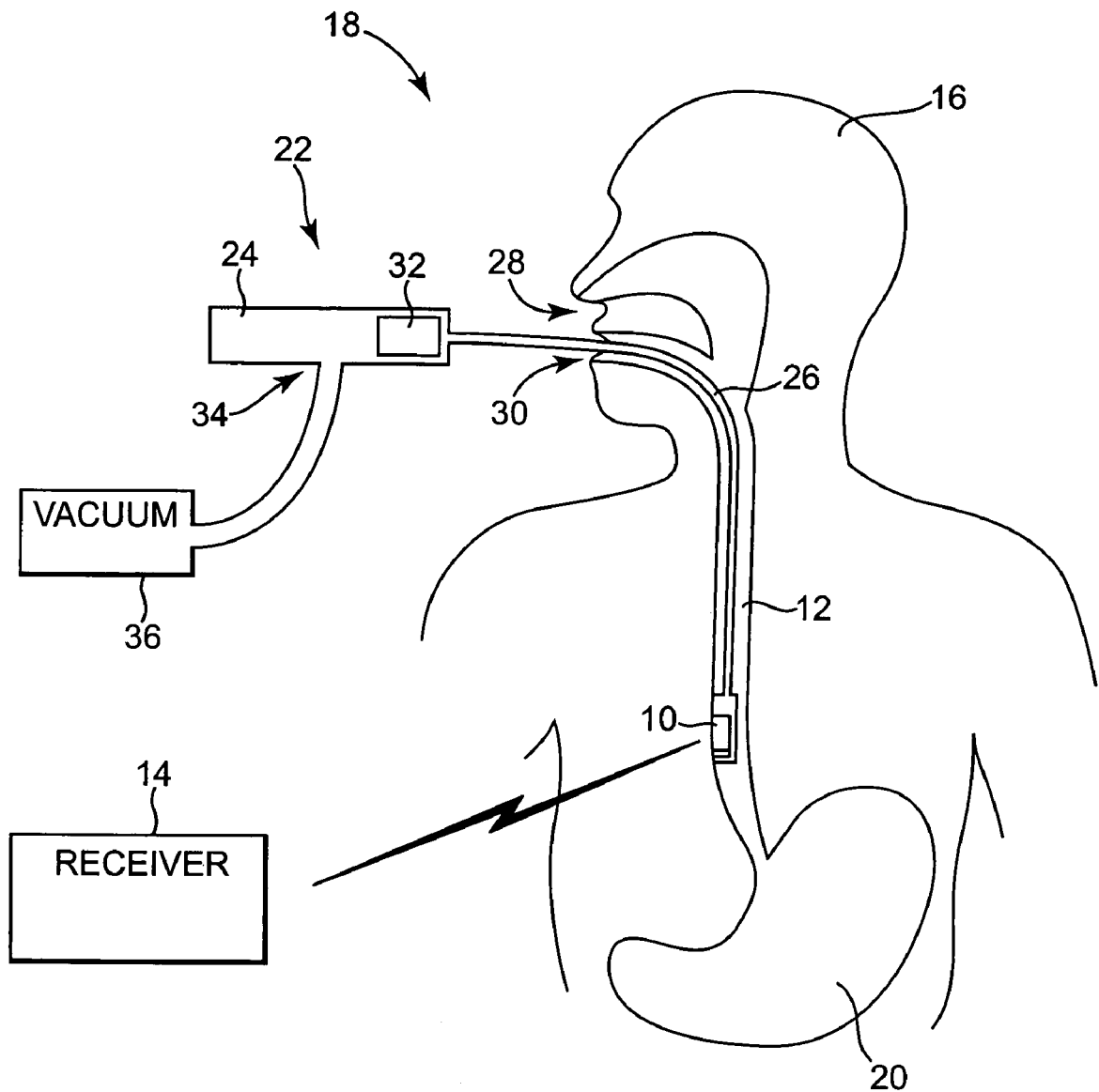
FIG. 2 is a schematic illustration of the placement of the remote pH monitor of FIG. 1.

FIG. 2 is another schematic diagram illustrating an acidity monitoring system 18 shown in conjunction with patient 16. Acidity monitoring system 18 measures the acidity within the lower portion of esophagus 12 of patient 16. More specifically, acidity monitoring system 18 measures the acidity level near the lower esophageal sphincter of patient 16, i.e., where esophagus 12 meets stomach 20. Measuring the acidity level of the lower portion of esophagus 12 allows a physician to more accurately diagnose Gastroesophageal Reflux Disease (GERD).

The lower esophageal sphincter normally relaxes to allow food to enter into stomach 20 from esophagus 12. The lower esophageal sphincter then contracts to prevent stomach acids from entering esophagus 12. In GERD, the lower esophageal sphincter relaxes too frequently or at inappropriate times allowing stomach acids to reflux into esophagus 12, increasing the acidity level near the lower portion of esophagus 12, which may lead to complications such as heartburn, painful swallowing, difficulty swallowing, coughing, wheezing, asthma, inflammation of the vocal cords or throat, esophageal ulcers, narrowing of the esophagus, and in the worst cases Barrett's esophagus.

Acidity monitoring system 18 includes a monitoring capsule 10 for sensing acidity and radio frequency receiver 14. Capsule 10 includes an acidity sensor, e.g., a pH sensor, to measure the acidity level within esophagus 12. Receiver 14 and capsule 10 are in wireless communication. In particular, capsule 10 transmits measured acidity data to receiver 14 via a transmitter and an antenna (not shown). Receiver 14 may, for example, comprise a portable receiver that is carried by patient 16. The information stored within receiver 14 may be downloaded by a physician to a computing device and analyzed to diagnose the condition of patient 16.

A delivery device 22 attaches capsule 10 to a wall of esophagus 12 and, more particularly, to esophageal tissue within esophagus 12. Delivery device 22 includes a proximal portion, referred to herein as a handle 24, and a flexible catheter 26 that extends from handle 24 into esophagus 12 of patient 16. Capsule 10 is coupled to a distal end of catheter 26 for delivery to a particular location within esophagus 12.

In particular, the distal end of catheter 26 enters esophagus 12, via either nasal cavity 28 or oral cavity 30 but preferably oral cavity 30, and extends through esophagus 12 into stomach 20 via the lower esophageal sphincter. The distal end of catheter 26 is slowly retracted back into esophagus 12 and the pressure variation due to the lower esophageal sphincter is detected to identify the appropriate location for capsule 10. Capsule 10 may be placed on a wall of esophagus 12 at the appropriate location.

Delivery device 22 includes a vacuum inlet 34 on handle 24 to couple delivery device 22 to a vacuum 36. Vacuum 36 applies suction within an inner lumen formed by catheter 26. A vacuum outlet (not shown) at the distal end of catheter 26 and, more particularly, at the interface between catheter 26 and capsule 10, applies the suction from vacuum 36 to the wall of esophagus 12 in order to draw esophageal tissue into a void within capsule 10. Delivery device 22 anchors capsule 10 to the esophageal tissue drawn into the void of capsule 10 and disengages from capsule 10, thereby leaving capsule 10 attached to the wall of esophagus 12. Delivery device 22 may, for example, advance a locking pin through the esophageal tissue drawn into the void to anchor capsule 10 to the wall of esophagus 12.

While on the wall of esophagus 12, capsule 10 and, more particularly, the acidity sensor of capsule 10 obtains acidity measurements for a period of time, e.g., 24 hours, and relays the acidity measurements to receiver 14 via wireless telemetry. Capsule 10 eventually self-detaches from the wall of esophagus 12 and is passed through the digestive system of patient 16.

Although the techniques of the invention are described in terms of delivering capsule 10 for sensing acidity of esophagus 12 of the patient, the techniques of the invention may be applied for delivery of other types of sensor to different tissue locations or organs.

It is preferred that capsule 10 be intubated trans-orally due to the size of capsule 10 itself. The larger size of capsule 10 makes it difficult intubate trans-nasally.

Accurate placement of capsule, or monitor, 10 is desirable in order to obtain accurate measurements and to aid in the diagnosis of GERD. However, as noted above, difficulties may arise in attempting to locate the lower esophageal sphincter trans-nasally. If trans-nasal manometry is attempted, it is difficult to translate the distance to the proper location determined trans-nasally to a distance needed to duplicate that location trans-orally. The distance to the proper location from the narres measured trans-nasally does not correlate well to the distance to the proper location from the incisors measured trans-orally. For this reason, it is desirable perform the manometry to find the proper location for the capsule through the same pathway used for the capsule. In other words, if the capsule is to be intubated trans-orally, then manometry to find the proper location for the capsule should also be done trans-orally.

Figure 3:
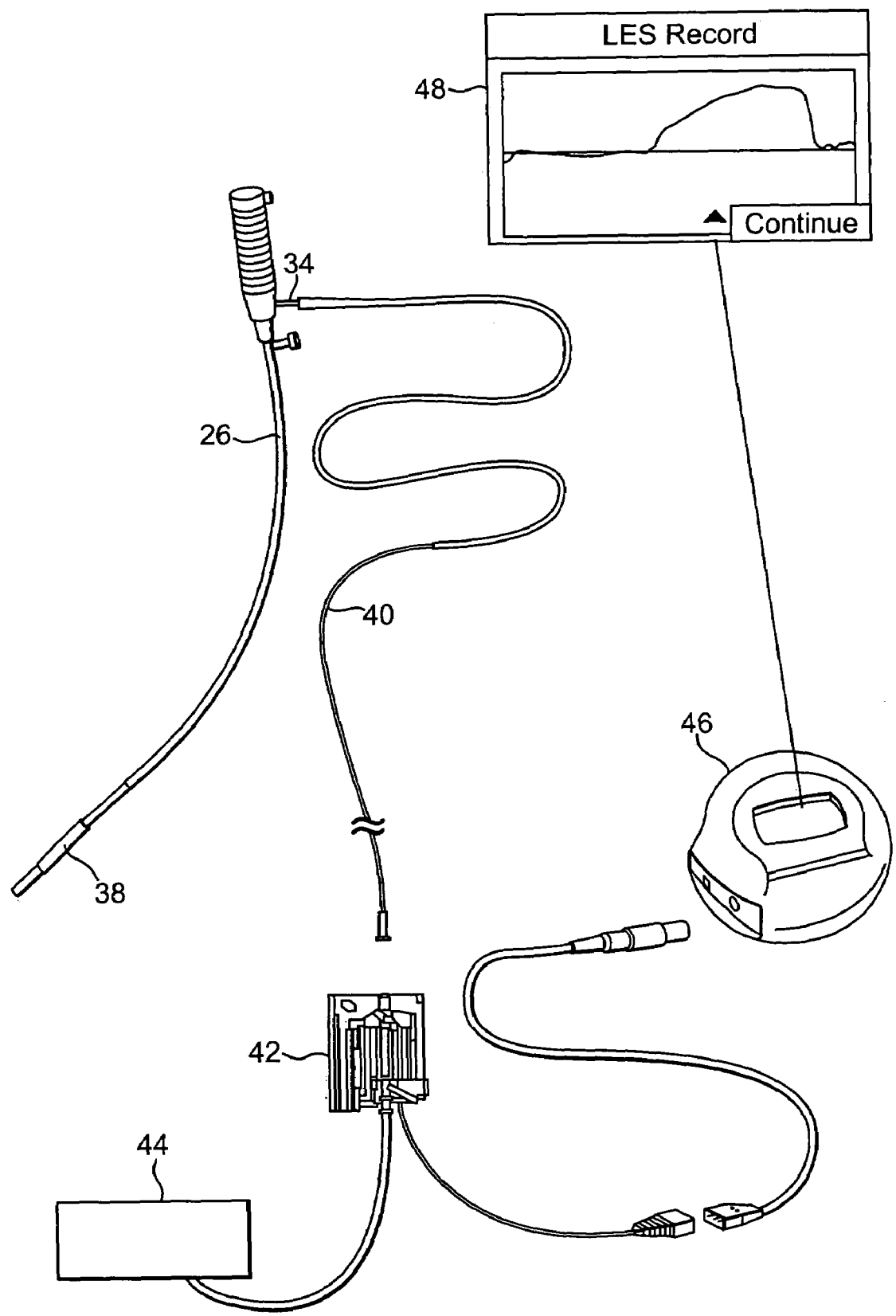
FIG. 3 is a schematic illustration of an apparatus for properly locating the remote pH monitor by identifying the upper boundary of the lower esophageal sphincter.

FIG. 3 schematically illustrates an embodiment of the present invention which can be used to determine the location of the upper boundary of the lower esophageal sphincter and, hence, aid in the placement of capsule 10. Catheter 26 has a distal end 38 designed to be intubated orally into esophagus 12 of patient 16. Handle 24 has what ordinarily is a vacuum inlet, or suction port, 34 used during delivery of capsule 10. To determine the proper location for capsule 10, extension line 40 couples suction port 34 to transducer 42. One port of transducer 42 is operatively coupled to a source of gas, for example air, 44 under constant pressure. A second port of transducer 42 is coupled to pressure meter 46. Transducer 42 can be a PDT 6000 System pressure transducer manufactured by Smith Medical/SIMS Deutschland, Kirchseeon, Germany. Pressure meter 46 can be a Digitrapper MkIII or a Digitrapper pH, both available from Medtronic, Inc., Minneapolis, Minn. Less expensive manometers can also be used, especially since only a relative pressure indication is required. Pressure meter 46 has a display 48 which can indicate a relative pressure provided by the gas in extension line 40 and, hence, catheter 26.

The present invention takes advantage of already existing catheter 26 which is used for the placement of capsule 10 trans-orally near the upper boundary of the lower esophageal sphincter. The same catheter 26 which will be used in placing capsule 10 can be intubated through esophagus 12 and lower esophageal sphincter into stomach 20, for example about 50 centimeters. The stomach 20 location can be verified by a positive pressure deflection while patient 16 takes a deep breath. Preferably, a pressure baseline is established with distal end 38 of catheter 26 positioned in stomach 20. The back pressure on the gas introduced through the lumen of catheter 26 will be relatively low in the relatively larger space of the stomach 20.

A gas, typically air, at a constant pressure is applied to one port of transducer 42 and ultimately to the lumen of catheter 26 while the distal end of catheter 26 is in the stomach 20. The introduction of positive gas pressure in the lumen of catheter 26 may assist in clearing out, or at least maintaining clearance, of the lumen of catheter 26 during the determination of the proper location of capsule 10.

The distal end of catheter 26 is then pulled backward, or out, through the lower esophageal sphincter, preferably one (1) centimeter at a time. At each one (1) centimeter interval, a pause is made and a relative pressure reading from pressure meter 46 is taken. As the distal end of catheter 26 passes through the relatively restricted area of the lower esophageal sphincter, a relatively higher pressure will be observed on the gas introduced into the lumen of catheter 26. Thus, the relative pressure exhibited by the gas introduced into the lumen of catheter 26 will at first increase due to the restriction caused by the lower esophageal sphincter and then decrease as the distal end of the catheter passes into esophagus 12. The decrease in pressure following the initial increase in pressure marks the location of the upper boundary of the lower esophageal sphincter. In a preferred embodiment, the relative pressure will drop below the baseline pressure and is indicative of the upper border of the lower esophageal sphincter.

The proper location for capsule 10 can then be determined relative to the identified location of the upper boundary of the lower esophageal sphincter. As an example, if it is desired to place the remote monitoring capsule approximately five (5) centimeters above the upper boundary of the lower esophageal sphincter, then catheter 26 would be pulled an additional five (5) centimeters from the esophagus. In some cases, the actual location of the monitoring device may be somewhat different than the location of outlet 38 of the lumen of catheter 26. For example, if the monitoring device is located two centimeters below outlet 38 of the lumen of catheter 26, then catheter 26 should be pulled up an additional two centimeters, or seven centimeters total, to properly place the monitoring device five centimeters above the upper boundary of the lower esophageal sphincter.

Following the identification of the proper location of capsule 10, catheter 26 used for the manometry to identify that location can be left in place and used according to the preceding techniques to insert and place capsule 10.

Due to the desired reuse of the lumen of catheter 26, liquid, principally water, based manometry is not desirable. Use of a foreign substance, such as water, leaves open the possibility that some the substance will still remain in the lumen of catheter 26 following the manometry. The presence of such foreign substance could possibly compromise the proper placement of capsule 10.

Thus a gas, usually air, is used in the trans-oral manometry using the same catheter 26 as will be used to place capsule 10. A gas, by it nature, is a compressible substance, and typically will provide less precise measurements in pressure than a more incompressible liquid. However, since only relative pressures are required to properly locate the upper boundary of the lower esophageal sphincter, air can be used with good results to properly locate the upper boundary of the lower esophageal sphincter.

Figure 4:
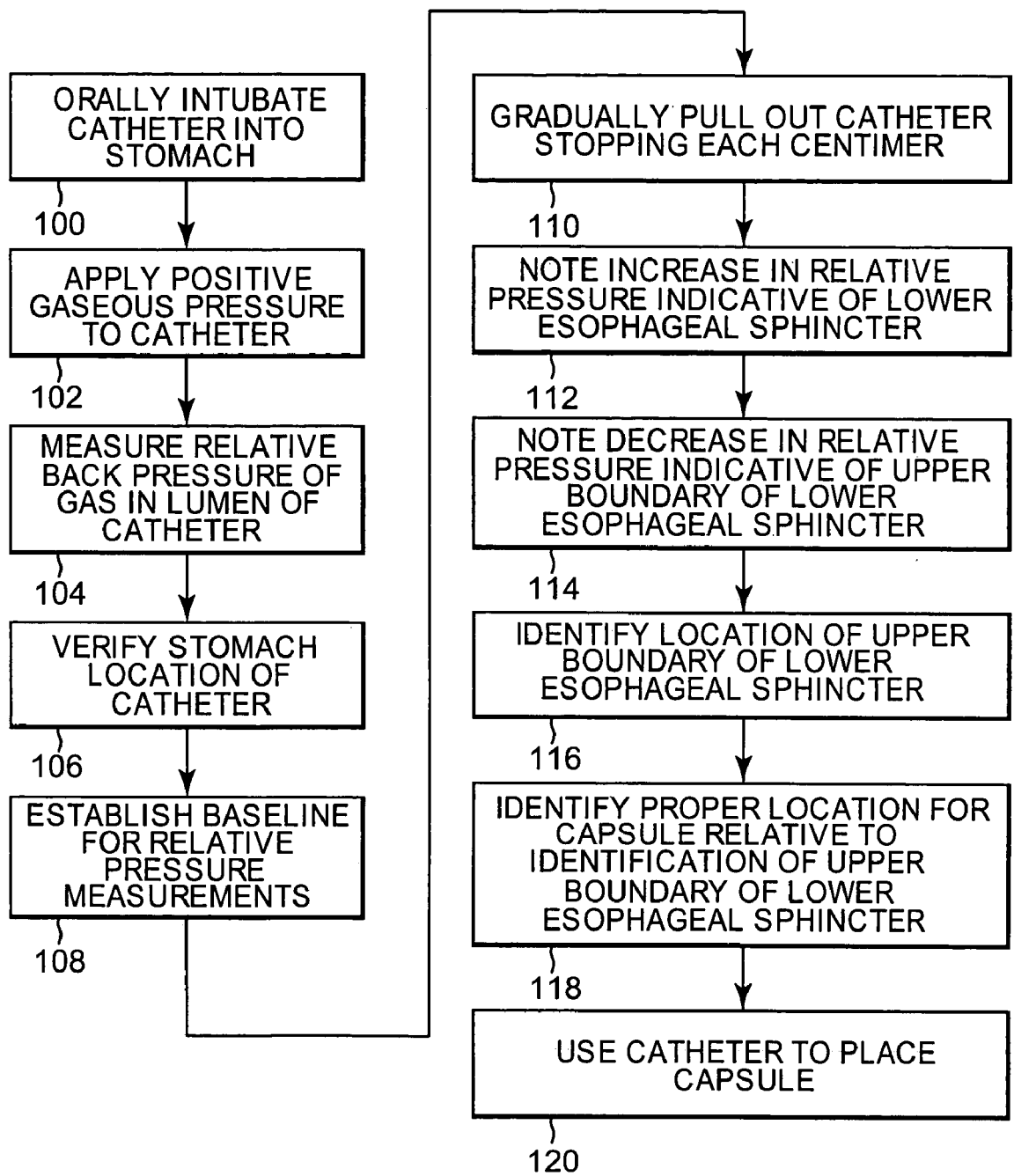
FIG. 4 is a flow chart of a method of identifying the upper boundary of the lower esophageal sphincter and placing the remote pH monitor of FIG. 1.

This method is illustrated diagrammatically in the flow chart of FIG. 4. Catheter 26 is orally intubated (100) through esophagus 12 into stomach 20 of patient 16. Positive gaseous pressure is applied (102) to catheter 26. A relative back pressure of the gas in catheter 26 is measured (104) until the upper boundary of the lower esophageal sphincter is identified (116). Optionally, the stomach 20 location of catheter 26 can be verified (106) by having patient 16 take a deep breath and noting a relative pressure increase. Optionally, a baseline is established (108) for relative pressure measurements. If this optional step is not performed, relative pressure measurements can still be noted by identifying changing pressure. Catheter 26 is gradually pulled out (110), preferably stopping approximately every centimeter. A distal end 38 of catheter 26 passes into the lower esophageal sphincter, the restricted area will register an increase in pressure. This increase is noted (112). As distal end 38 of catheter 26 passes past the upper boundary of lower esophageal sphincter into esophagus 12, a decrease in pressure will be observed. This decrease is noted (114). At this decrease in pressure, the upper boundary of the lower esophageal sphincter is identified (116). From this identification, a proper location for capsule 10 can be determined (118) using a direct measurement from the upper boundary of the lower esophageal sphincter. Following the proper identification of the proper location of capsule 10, catheter 26 is then used to properly place capsule 10 in esophagus 12.

While the invention has been described in detail as applying to the human esophagus and as applying to locating the upper boundary of the lower esophageal sphincter, it is to be recognized and understood that the present invention is not so limited. The present invention may find usefulness in application to other body cavities, such as those of the stomach, colon, rectum, bladder, uterus, vagina, billiary ducts and blood vessels.

Thus, embodiments of the apparatus for determining a location in a body using a catheter and method of using such catheter are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of using an esophageal catheter, having a lumen, comprising the steps of:
    determining an esophageal location in a patient having an esophagus, comprising the steps of:
        passing a distal end of said catheter through an esophagus and a lower esophageal sphincter into a stomach of a patient;
        introducing a flow of gas having a constant pressure to a proximate end of said lumen of said esophageal catheter;
        measuring a lumen pressure of said gas in said lumen;
        pulling back said distal end of said catheter from said patient;
        noting an increase in said lumen pressure;
        noting a subsequent decrease in said lumen pressure;
        identifying an upper boundary of said lower esophageal sphincter based upon said decrease; and
        establishing said esophageal location relative to said upper boundary of said lower esophageal sphincter; and
    anchoring a capsule to said esophagus with said catheter.

2. A method as in claim 1 further comprising the step of determining a baseline for said lumen pressure before said pulling back step and wherein said increase in said lumen pressure is relative to said baseline.

3. A method as in claim 2 wherein said distal end of said catheter is removed gradually.

4. A method as in claim 3 wherein said increase is measured as said distal end of said catheter enters said lower esophageal sphincter.

5. A method as in claim 4 wherein said decrease is measured as said distal end of said catheter passes an upper boundary of said lower esophageal sphincter.

6. A method as in claim 5 wherein said anchoring step is accomplished by measuring a predetermined distance from said upper boundary of said lower esophageal sphincter.

7. A method as in claim 6 wherein said esophageal location is a predetermined distance above said upper boundary of said lower esophageal sphincter.

8. A method as in claim 1 wherein said pulling back step is accomplished in a series of incremental steps with pauses in between each of said incremental steps and wherein said measuring step is accomplished during said pauses.

9. A method as in claim 1 wherein said gas comprises air.

10. A method of using a catheter having a lumen, comprising the steps of:
    determining an esophageal location in a patient having an esophagus, comprising the steps of:
        passing a distal end of said catheter through a first chamber and a restriction into a second chamber of a patient;
        introducing an air flow having a constant pressure to a proximate end of said lumen;
        measuring a lumen pressure in said lumen;
        determining a baseline for said lumen pressure;
        pulling back said distal end of said catheter from said patient;
        noting an increase in said lumen pressure;
        noting a subsequent decrease in said lumen pressure;
        identifying an upper boundary of said restriction upon said decrease; and
    establishing said esophageal location relative to said upper boundary of said lower esophageal sphincter; and
    anchoring a capsule to said esophagus with said catheter.

11. A method as in claim 10 further comprising the step of determining a baseline for said lumen pressure before said pulling back step and wherein said increase in said lumen pressure is relative to said baseline.

12. A method as in claim 11 wherein said distal end of said catheter is removed gradually.

13. A method as in claim 12 wherein said increase is measured as said distal end of said catheter enters said restriction.

14. A method as in claim 13 wherein said decrease is measured as said distal end of said catheter passes an upper boundary of said restriction.

15. A method as in claim 14 wherein said anchoring step is accomplished by measuring a predetermined distance from said upper boundary of said restriction.

16. A method as in claim 15 wherein said esophageal location is a predetermined distance above said upper boundary of said restriction.

17. A method as in claim 10 wherein said pulling back step is accomplished in a series of incremental steps with pauses in between each of said incremental steps and wherein said measuring step is accomplished during said pauses.

18. A method as in claim 10 wherein said gas comprises air.

* * * * *